US00PP37413P2

(12) United States Plant Patent
Langella

(10) Patent No.: US PP37,413 P2
(45) Date of Patent: May 5, 2026

(54) ***CAMPANULA* PLANT NAMED 'KLECN23088'**

(50) Latin Name: ***Campanula portenschlagiana* Schult. x *Campanula poscharskyana* Degen**
Varietal Denomination: KLECN23088

(71) Applicant: KLEMM + SOHN GMBH & CO. KG, Stuttgart (DE)

(72) Inventor: Raffaele Langella, Fiumicino (IT)

(73) Assignee: KLEMM+ SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/227,971

(22) Filed: Jun. 4, 2025

(51) Int. Cl.
*A01H 5/02* (2018.01)
*A01H 6/26* (2018.01)

(52) U.S. Cl.
USPC ..... Plt./414

(58) Field of Classification Search
USPC ..... Plt./414
See application file for complete search history.

(56) References Cited

PUBLICATIONS

CPVO Application Consultation, version 4.23.11; citation for *Campanula* 'KLECN23088' (Retrieved on Sep. 8, 2025).*

* cited by examiner

*Primary Examiner* — Susan McCormick Ewoldt
(74) *Attorney, Agent, or Firm* — Weatherly IP Solutions, LLC; Karen P. Bechtold; James M. Weatherly

(57) ABSTRACT

A new *Campanula* plant particularly distinguished by an upright to outwardly, compact, dense and bushy plant habit, very high and freely branching with compact, flat habit, early flowering habit; and Campanulate-shaped flowers with dark violet-colored petals, is disclosed.

1 Drawing Sheet

Genus and species: *Campanula portenschlagiana* Schult. x *Campanula poscharskyana* Degen.
Variety denomination: 'KLECN23088'.

BACKGROUND OF THE NEW PLANT

The present invention comprises a new and distinct variety of *Campanula*, botanically known as *Campanula portenschlagiana* Schult. x *Campanula poscharskyana* Degen and hereinafter referred to by the variety name 'KLECN23088'. 'KLECN23088' originated from an open cross-pollination in June 2020 in Stuttgart, Germany between a proprietary unnamed female *Campanula portenschlagiana* (unpatented) and a proprietary unnamed male *Campanula poscharskyana* (unpatented).

The seeds from the cross were collected and sown in Stuttgart, Germany in the summer of 2020 and the plants were grown for evaluation. An individual plant designated 'KLECN23088' was selected in autumn 2020 in Stuttgart, Germany. In the autumn 2021 'KLECN23088' was first vegetatively propagated by vegetative terminal cuttings in Stuttgart, Germany. 'KLECN23088' was found to reproduce true to type in successive generations of asexual propagation via vegetative cuttings.

SUMMARY

The following are the most outstanding and distinguishing characteristics of this new variety when grown under normal horticultural practices in Stuttgart, Germany.

1. Upright to outwardly, compact, dense and bushy plant habit.
2. Very high and freely branching with compact, flat habit.

3. Early flowering habit.
4. Campanulate-shaped flowers with dark violet-colored petals.

DESCRIPTION OF THE PHOTOGRAPH

This new *Campanula* plant is illustrated by the accompanying photograph which shows a close-up of the foliage, buds, and mature flower. The photograph is of a 12-week-old plant grown indoors in Stuttgart, Germany in April 2023. The colors shown are as true as can be reasonably obtained by conventional photographic procedures.

DESCRIPTION OF THE NEW VARIETY

The following detailed descriptions set forth the distinctive characteristics of 'KLECN23088'. The data which define these characteristics were collected in Stuttgart Germany in May 2025 on 10-week-old plants. References are to The R.H.S. Colour Chart of The Royal Horticultural Society of London (R.H.S.), 5$^{th}$ edition (2007).

Classification:
*Family*.—Campanulaceae.
*Botanical*.—*Campanula portenschlagiana* Schult. x *Campanula poscharskyana* Degen.
*Common*.—*Campanula*.
*Designation*.—'KLECN23088'.

Parentage:
*Female parent*.—Unnamed selection of *Campanula portenschlagiana*, not patented.
*Male parent*.—Unnamed selection of *Campanula poscharskyana*, not patented.

Plant:

*Asexual propagation.*—By cuttings.

*Form.*—Compact, globular, mounding, densely branching.

*Habit.*—Very high and freely branching with compact, flat habit.

*Roots.*—Fine, well branched; white in color (RHS NN155A).

*Height (from soil line to top of foliage).*—6.0 cm to 8.0 cm.

*Spread.*—14.0 cm to 18.0 cm.

Propagation:

*Type cuttings.*—Unrooted cuttings; terminal vegetative cuttings, from stock plants maintained at short days.

*Time to produce a rooted cutting.*—About 26 to 28 days at 19° C. to 21° C.

*Pest and disease resistance.*—Under commercial production conditions, plants of the new *Campanula* have not been noted to be resistant to pathogens or pests common to *Campanula.*

Stems:

*Average number of stems.*—30 to 50.

*Stem color.*—RHS 144B.

*Pubescence.*—Absent.

*Pubescence color.*—N/A.

*Stem description.*—Strong stem branched up to 10 to 12 sub-branches each carrying flowers.

*Stem diameter.*—0.2 cm to 0.3 cm.

*Stem length.*—8 cm to 15 cm. From soil line to first node: 0.5 cm to 1.0 cm. Total length: 8.0 cm to 15.0 cm.

*Internode length.*—0.4 cm to 0.8 cm.

*Anthocyanin.*—Absent.

*Color.*—RHS 145A.

Leaves:

*Description.*—Simple.

*Arrangement.*—Alternate.

*Shape.*—Cordate.

*Apex.*—Acute to acuminate.

*Base.*—Truncate to cordate.

*Margin.*—Broadly dentate-ondulate.

*Length.*—1.0 cm to 1.6 cm.

*Width.*—1.1 cm to 1.5 cm.

*Texture.*—Upper surface: Slightly rugose. Lower surface: Slightly rugose.

*Pubescence.*—Upper surface: Smooth. Lower surface: Smooth.

*Color.*—Young leaf expanding: Upper surface: RHS N137B. Lower surface: RHS 147B. Mature leaves: Upper surface: RHS N137A. Lower surface: RHS 137B.

*Veins.*—Vein color: Upper surface: RHS 147B. Lower surface: RHS 147B.

Petiole:

*Description.*—All leaves are petiolate.

*Average length.*—3.0 cm to 3.5 cm.

*Average diameter.*—1.0 mm.

*Shape.*—Semi-cylindrical with the flat part facing upwards.

*Texture.*—Rarely pubescent.

*Color.*—Upper surface: RHS 137B. Lower surface: RHS 144A.

Inflorescence:

*Flowering type.*—Single star-shaped tubular-campanulate.

*Flowering requirements.*—8 to 9-weeks of long daytime conditions.

*Flowering season.*—May to October under natural light conditions.

*Duration of flowers.*—3 to 9 days depending on temperature.

*Description.*—At apex; attitude rounded to slightly outright.

*Height.*—12.0 to 16.0 cm.

*Width.*—6.0 to 8.0 cm.

Flower:

*Description.*—Single star-shaped campanulate flowers arranged in panicles.

*Length.*—1.8 cm to 2.1 cm (top to the base of corolla).

*Width.*—2.1 cm to 2.4 cm.

*Fragrance.*—Not detected.

*Number of flowers.*—Per stem: 30 to 60. Per plant: 1000 to 2500 (buds to open flowers).

Flower buds:

*Shape.*—Ovate, elliptic.

*Apex.*—Acuminate to rounded.

*Base.*—Rounded.

*Length.*—0.5 mm to 1.5 mm.

*Width.*—0.2 mm to 0.32 mm.

*Flower bud color.*—RHS 144A a slight tinge of RHS 86A with RHS N88A on upper parts of opening corolla.

Petals:

*Description.*—Five petals in a single whorl, fused at the base, star shaped.

*Shape.*—Lanceolate.

*Apex.*—Acute.

*Base.*—Fused with other petals.

*Margin.*—Entire.

*Length.*—1.8 cm to 2.2 cm.

*Width.*—0.4 cm to 0.55 cm.

*Texture.*—Smooth.

*Pubescence.*—Absent.

*Petal color.*—Upper surface: RHS N88A. Lower surface: RHS N88B and RHS N88A.

Corolla:

*Description.*—Five petals in a single whorl, fused at the base, star shaped.

*Length.*—1.5 cm to 1.7 cm.

*Width.*—1.8 cm to 2.3 cm.

*Shape.*—Lanceolate.

*Lobes.*—Length: 2.5 cm to 2.8 cm. Width: 0.5 cm to 0.6 cm.

Sepal:

*Number.*—5.

*Shape.*—Five sepals in a single whorl, fused at the base; star-shaped.

*Apex.*—Acute-acuminate.

*Base.*—Fused.

*Margin.*—Entire.

*Length.*—0.6 cm to 0.8 cm.

*Width.*—0.1 cm to 0.2 cm.

*Texture.*—Upper surface: Smooth, glabrous. Lower surface: Smooth, glabrous.

*Color.*—Upper surface: RHS N146B with a slight tinge of RHS 81A on edges. Lower surface: RHS N146A with a slight tinge of RHS 81A on edges.

*Peduncle.*—Number per plant: 50 to 60. Description: Robust panicle, straight with upright tendency. Shape: Semi-cylindrical shape. Texture: Smooth, rare pubescence. Attitude: Straight, upright to outward. Strength: Robust. Length: 12.0 cm to 15.0 cm. Width: 0.16 cm to 0.22 cm. Average number of nodes: 12 to 28. Internode spacing: 0.5 cm to 1.0 cm. Branching description: Densely branching, well distributed forming compact, mounding shaped plants. Color: RHS 145A.

*Pedicel*.—Shape: Straight. Length: 0.3 cm to 0.5 cm. Width: 0.05 cm to 0.1 cm. Texture: Rarely pubescence. Color: RHS 144A.

Androecium:

*Number*.—5.

*Filament*.—Description: Enlarged at base. Length: 0.2 cm to 0.3 cm. Width: 0.15 at the base to 0.05 cm. Color: RHS 155B.

*Anther*.—Description: Linear. Length: 0.5 cm to 0.6 cm. Width: 0.05 cm. Color: RHS 4D.

*Pollen*.—Amount: Low to moderate quantity. Color: RHS 19D.

*Gynoecium*.—Description: Gynoecium with superior, globular-pyramidal ovary. Length: 1.2 cm to 1.5 cm.

*Style*.—Shape: Straight. Length: 0.9 cm to 1.0 cm. Width: 0.05 cm to 0.08 cm. Color: RHS 91B.

*Stigma*.—Description: Tripartite. Length: 0.2 cm to 0.3 cm. Width: 0.02 cm to 0.03 cm. Color: RHS 92A.

*Ovary*.—Shape: Globular-pyramidal. Length: 0.15 cm. Width: 0.2 cm to 0.25 cm. Color: RHS 145D.

*Calyx*.—Length: 0.8 cm to 0.9 cm. Width: 0.7 cm to 0.8 cm.

Seed:

*Shape*.—Elliptic.

*Length*.—0.06 cm to 0.08 cm.

*Width*.—0.03 cm to 0.04 cm.

*Texture*.—Shiny, smooth.

*Color*.—RHS 177A.

Cold hardiness: Specific zone hardiness not determined.

COMPARISON WITH PARENTAL LINES AND KNOWN VARIETY

'KLECN23088' is a distinct variety of *Campanula* and is distinguished from its parents as described in Table 1.

TABLE 1

Comparison with Parental Lines

| Characteristic | 'KLECN23088' | Female Parent | Male Parent |
|---|---|---|---|
| Earliness (time to plant flowering) | 9 weeks (14 hours of daylight) | 1 week earlier than 'KLECN23088' | 2 weeks later than 'KLECN23088' |
| Flower color | Dark violet | Lighter color than 'KLECN23088' | Darker color than 'KLECN23088' |
| Growth habit | Flat-mounding, outwards growing | Flat growing | Bushy growing |
| Leaf color | Dark Green | Dark green | Normal green |

'KLECN23088' is most similar to the commercial *Campanula* variety Campala® 'Nina' (patent status unknown). Differences between the varieties are described in Table 2.

TABLE 2

Comparison with Similar Variety

| Characteristic | 'KLECN23088' | Commercial variety 'Nina' |
|---|---|---|
| Corolla color | Darker color than Commercial variety 'Nina' | Lighter color than 'KLECN23088' |
| Shape of plant | More flat-rounded | More upright |
| Branching | More branching | Less branching |
| Earliness (time to plant flowering) | 14 days later than Commercial variety 'Nina' | 14 days earlier than 'KLECN23088' |

I claim:

1. A new and distinct variety of *Campanula* plant designated 'KLECN23088' as illustrated and described herein.

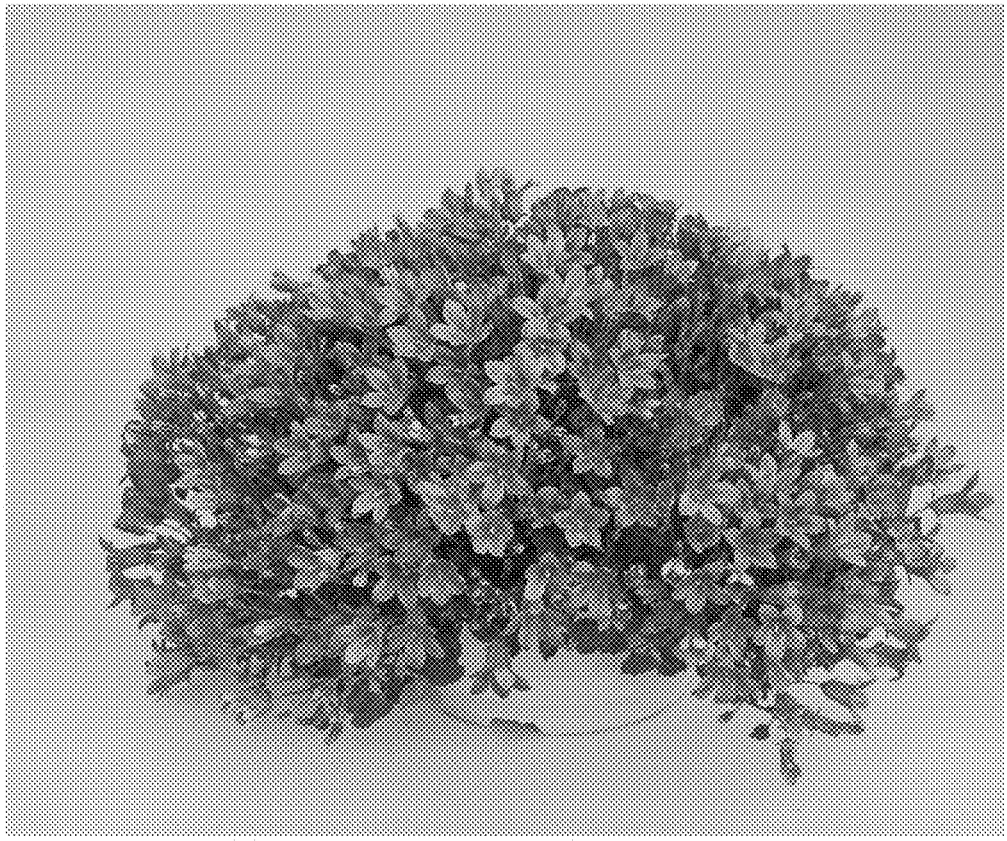

* * * * *